United States Patent [19]

Desai

[11] Patent Number: 5,756,125
[45] Date of Patent: May 26, 1998

[54] CONTROLLED RELEASE NAPROXEN SODIUM PLUS NAPROXEN COMBINATION TABLET

[75] Inventor: Subhash Desai, Grayslake, Ill.

[73] Assignee: G. D. Searle & Co., Chicago, Ill.

[21] Appl. No.: 457,415

[22] Filed: Jun. 1, 1995

Related U.S. Application Data

[63] Continuation-in-part of Ser. No. 937,920, Aug. 31, 1992, Pat. No. 5,609,884.

[51] Int. Cl.⁶ .................................................. A61K 9/22
[52] U.S. Cl. ........................ 424/468; 424/464; 424/465; 424/469; 424/457
[58] Field of Search ......................... 424/468, 464, 424/482, 489, 480, 409

[56] References Cited

U.S. PATENT DOCUMENTS

| | | | |
|---|---|---|---|
| 4,571,333 | 2/1986 | Hsiao et al. | 424/22 |
| 4,599,359 | 7/1986 | Cooper | 514/557 |
| 4,704,406 | 11/1987 | Stanislaus et al. | 514/570 |
| 4,794,112 | 12/1988 | Cooper | 514/255 |
| 4,803,079 | 2/1989 | Hsiao et al. | 424/468 |
| 4,888,178 | 12/1989 | Rotini et al. | 424/468 |
| 4,888,179 | 12/1989 | Rotini et al. | 424/468 |
| 4,920,149 | 4/1990 | Sunshine et al. | 514/557 |
| 4,923,898 | 5/1989 | Sunshine et al. | 514/557 |
| 5,043,167 | 8/1991 | Rotini et al. | 424/490 |
| 5,055,306 | 10/1991 | Barry et al. | 424/482 |
| 5,093,200 | 3/1992 | Watanabe et al. | 424/468 |
| 5,378,474 | 1/1995 | Morella et al. | 424/469 |
| 5,425,950 | 6/1995 | Dandiken et al. | 424/480 |
| 5,480,650 | 1/1996 | Marchi et al. | 424/464 |

FOREIGN PATENT DOCUMENTS

| | | | |
|---|---|---|---|
| 0 274 734 A1 | 7/1988 | European Pat. Off. | A61K 9/24 |
| 0 438 249 A1 | 7/1991 | European Pat. Off. | A61K 31/19 |

*Primary Examiner*—Thurman K. Page
*Assistant Examiner*—William E. Benston, Jr.
*Attorney, Agent, or Firm*—Cynthia S. Kovacevic; Roger A. Williams

[57] ABSTRACT

The present invention relates to controlled release dosage forms composed of a naproxen layer which contains a delayed release granulate of naproxen compressed with an immediate release granulate of naproxen and an immediate release naproxen sodium layer compressed with the naproxen layer, designed to promptly exert a therapeutic effect while also maintaining the therapeutic blood concentration for a prolonged duration of 24 hours.

14 Claims, 3 Drawing Sheets

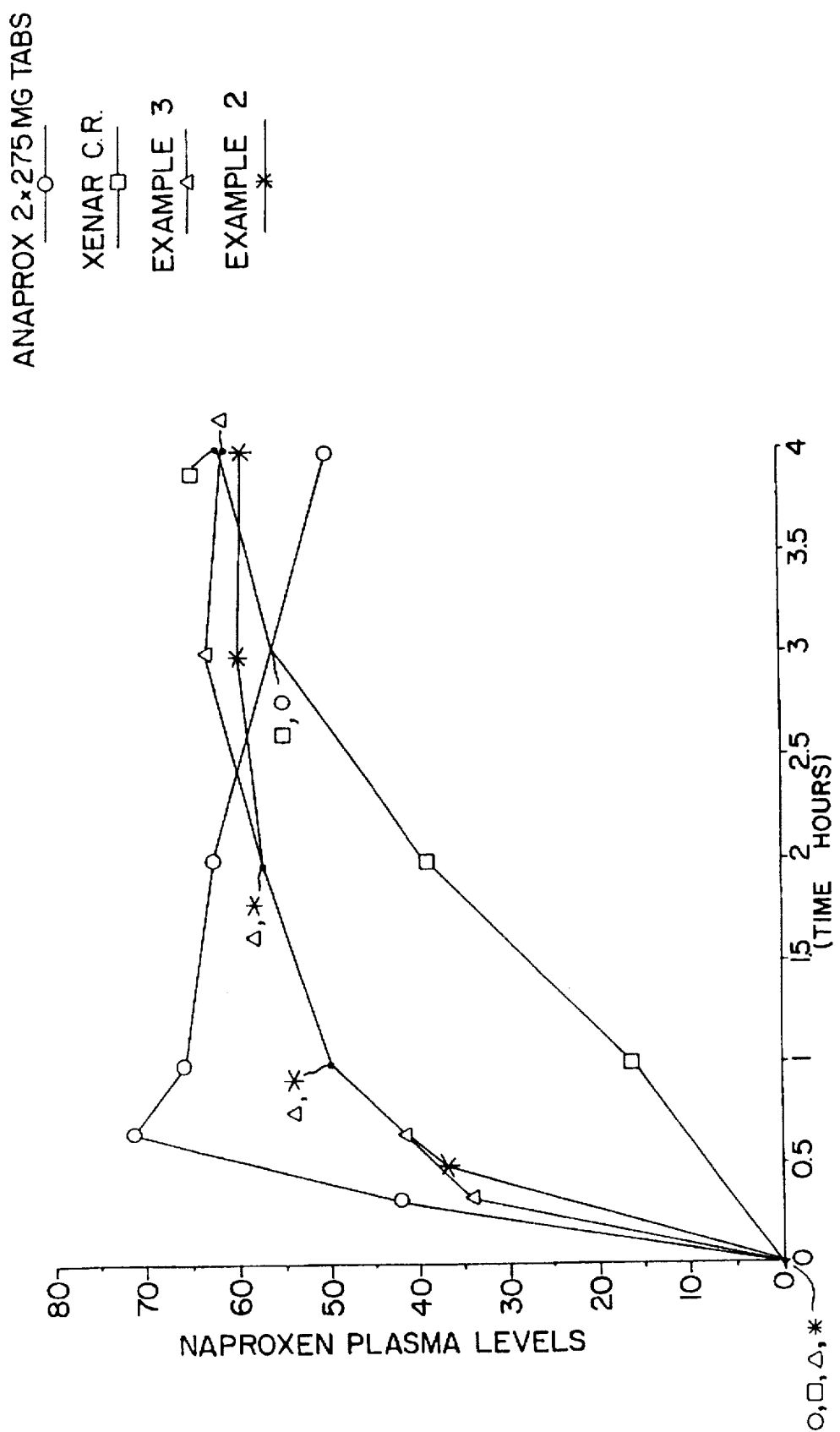

CONTROLLED RELEASE NAPROXEN SODIUM PLUS NAPROXEN COMBINATION TABLET

This is a CONTINUATION IN PART of Application Ser. No. 07/937,920, filed Aug. 31, 1992, now U.S. Pat. No. 5,609,884.

BACKGROUND OF THE INVENTION

The invention herein is directed to new controlled release multi-layer pharmaceutical compositions containing a combination of naproxen and naproxen sodium. The first layer of the pharmaceutical composition consists of delayed release granulates of naproxen compressed together with immediate release granulates of naproxen. A layer of immediate release naproxen sodium is compressed onto the first layer of naproxen forming an adjacent layer or layers.

Naproxen, [(S)-6-methoxy-α-methyl-2-naphthaleneacetic acid, hereinafter also referred to as naproxen acid] is of the formula

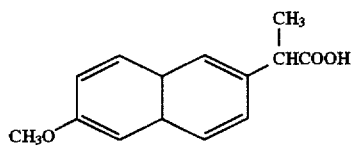

Naproxen is widely used (in such an acid state) as an anti-inflammatory compound in the treatment of arthritis, and as an analgesic and antipyretic in the treatment of mild to moderate pain, such as dysmenorrhea or arthritis.

Naproxen has a low water solubility and a comparatively slow rate of absorption which is a disadvantage when using naproxen as an analgesic. This drawback is overcome by the use of its salt, naproxen sodium. Naproxen sodium is the sodium salt of naproxen acid. Naproxen sodium, due to its higher water solubility, has a comparatively faster rate of absorption leading to a prompt analgesic and antipyretic effect. Hence, naproxen sodium is the drug of choice in the treatment of mild to moderate pain where a prompt therapeutic effect is desired. After absorption, both naproxen and naproxen sodium exist in the circulating blood as naproxen anions.

Naproxen is available in 250 mg, 375 mg and 500 mg tablets and is generally administered in therapeutic doses of 500-1000 mg per day, while naproxen sodium is available in 275 mg and 550 mg tablets and is administered in therapeutic doses of 550-1100 mg per day. Both compounds have multiple frequencies of administration of 8-12 hours every day.

Conventional dosage forms of naproxen or naproxen sodium are administered two to three times daily to maintain therapeutic blood levels which results in a large fluctuation in peak and trough blood levels. Controlled release dosage forms for naproxen have been designed to overcome this drawback by reducing the fluctuation and maintaining the desired therapeutic blood concentration as well as reducing the frequency of drug administration.

Hsias and Kent (U.S. Pat. Nos. 4,571,333 and 4,803,079) disclose the use of controlled release naproxen formulations and disclose the use of controlled release naproxen sodium formulations. Therapeutic blood peak levels of naproxen are not achieved promptly by these formulations and take greater than 6 hours to be achieved, as indicated by the maximum concentrations ($C_{max}$) disclosed therein.

Rotini and Marchi (U.S. Pat. No. 4,888,178) disclose galenic formulations made of a mixture of immediate release naproxen granulate and a controlled release naproxen granulate. Naproxen, in its acid form (naproxen acid), is used in both the immediate release granulate and the controlled release granulate.

Although the concept of using either naproxen or naproxen sodium independently in controlled release dosage forms has been demonstrated, the art available has several disadvantages. First, the relevant art demonstrates that therapeutic blood levels, as indicated by the maximum concentration ($C_{max}$) are not achieved promptly to exert a fast therapeutic response. Such a delay in reaching therapeutic blood levels is unsuitable for use as an analgesic and antipyretic in the treatment of mild to moderate pain such as dysmenorrhea or arthritis, where fast onset of action is necessary to obtain pain relief.

Furthermore, utilizing naproxen sodium alone in a controlled release system disclosed in the relevant art results in failure to maintain therapeutic blood concentration for a prolonged duration of 24 hours since its higher solubility will not delay the release of the compound from the dosage form at a rate comparable to naproxen.

In addition, matrix systems described in the art are designed to remain intact, and since naproxen and naproxen sodium are known to be irritants to the gastrointestinal tract, such systems may not empty from the stomach due to its large size. The retention of such systems in the stomach may thereby cause gastric damage.

It would be desirable to provide a pharmaceutical composition that achieves a therapeutic blood level of naproxen anions promptly to exert a fast therapeutic analgesic effect, which composition also maintains the therapeutic blood concentration for a prolonged duration of 24 hours being therefore suitable for once a day administration and which does not remain intact as a matrix.

SUMMARY OF THE INVENTION

The present invention relates to controlled release preparations containing a combination of naproxen sodium and naproxen acid. Specifically, it relates to a multilayer oral dosage form comprising a layer of naproxen comprised of a delayed release granulate of naproxen compressed with an immediate release granulate of naproxen. The delayed release naproxen is a mixture of naproxen with retarding agents, hydrogenated castor oil and ethylcellulose. The immediate release naproxen is a granulate of naproxen.

The compressed delayed release naproxen and immediate release naproxen (hereinafter the naproxen layer) are then compressed with a layer of immediate release naproxen sodium granulate (hereinafter the naproxen sodium layer). The tablet is designed to provide prompt therapeutic plasma levels of naproxen in less than 1 hour and maintain these levels for a duration of 24 hours, thereby providing for once daily administration. The tablet is designed to disintegrate, rather than remain as a matrix in the stomach, thereby reducing the potential for gastric irritation and variability in absorption.

The invention herein will be more fully understood with regard to the following brief description of the accompanying drawings and the following detailed description of the invention.

BRIEF DESCRIPTION OF THE DRAWINGS

FIG. 5 is a graphical representation of the plasma profiles of two different naproxen and naproxen sodium controlled formulations, of an immediate release naproxen sodium formulation and of a controlled release naproxen acid formulation, over the initial four hours following administration.

DETAILED DESCRIPTION OF THE INVENTION

Figure 1:
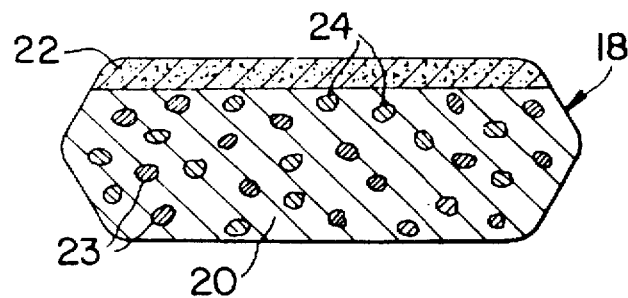
FIG. 1 is a cross sectional representation of a tablet of the pharmaceutical composition described herein.

The present invention is directed to multilayer controlled release preparations containing a layer of compressed delayed and immediate release granulates of naproxen and a layer of naproxen sodium. Such a dosage form, immediately releasing naproxen sodium, provides a fast rate of absorption, achieving a desired therapeutic plasma level in less than 1 hour. The subsequent disintegration and release of the immediate and delayed release granulates of naproxen maintains the therapeutic blood levels for a duration of 24 hours, thereby providing once daily administration. The compositions achieve a therapeutic effect which is prompt and maintained for a longer duration while disintegration of the tablet reduces gastric retention time thereby reducing the potential for gastric irritation and damage. The compositions reduce variability of absorption of naproxen thereby leading to predictable bioavailability.

As used herein the terms "multilayer" or "multilayered" encompass tablets consisting of two or more adjacent layers, including but not limited to, bilayer and trilayer tablets and compositions consisting of a coating surrounding an inner core. Types of multilayer pharmaceutical compositions and methods of manufacturing such compositions are well known in the pharmaceutical art. The terms "core" or "coating" are used herein synonymously with the term "layer" which is further described in the detailed description of the drawings herein.

The precise amounts of naproxen sodium and naproxen needed to achieve therapeutic blood concentration are calculated by means of pharmacokinetic modelling and pharmacodynamic response. (See Thomson et al., *Clin. Pharmacol. Ther.*, February 1981, 29(2) p. 168–73 for plasma concentration profiles.)

More specifically, the present invention is a controlled release pharmaceutical composition containing naproxen sodium present in an amount from about 15 to about 70 w/w % of the compositions of the present invention, more preferably from about 20 to about 50 w/w %, more preferably from about 30 to about 35 w/w % and most preferably about 33 to 34% w/w %.

Preferably, the percent of naproxen acid present in the pharmaceutical composition of the present invention is from about 20 to about 70 w/w % of the compositions of the present invention, more preferably from about 40–80 w/w % and most preferably about 40 w/w %.

The percent of naproxen acid present in the immediate release granulate of the naproxen acid layer is up to about 10 w/w %, more preferably from about 1 to about 5 w/w % and most preferably about 4.5 w/w %. The percent of naproxen acid present in the controlled release granulate of the naproxen acid layer is from about 20 to about 50 w/w % and most preferably about 35.5 w/w %.

A total composition is formed from a mixture of:
54.3 w/w % naproxen;
14.4 w/w % naproxen sodium;
1.8 w/w % lactose;
18.3 w/w % hydrogenated castor oil;
5.8 w/w % ethyl cellulose;
3.6 w/w % polyvinylpyrrolidone; and
1.8 w/w % other pharmaceutically acceptable excipients and lubricating agents.

Preferably the total composition is formed from a mixture of 40.1 w/w % naproxen; 33.9 w/w % naproxen sodium; 7.1 w/w % lactose hydrous; 13.5 w/w % hydrogenated castor oil; 4.3 w/w % ethyl cellulose and 1.1 w/w % other pharmaceutically acceptable excipients and lubricating agents.

Figure 2:
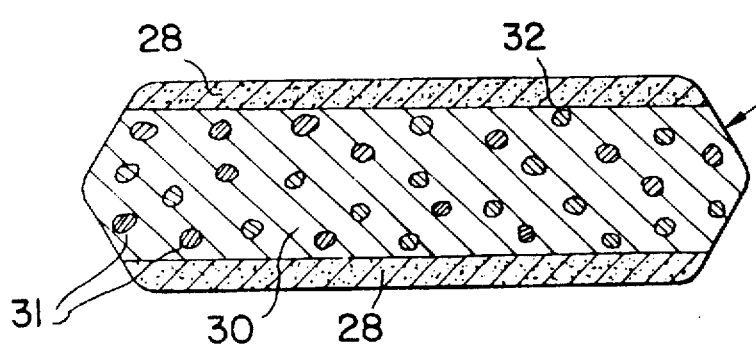
FIG. 2 is a cross sectional representation of a second embodiment of a tablet of the pharmaceutical composition described herein.
Figure 3:
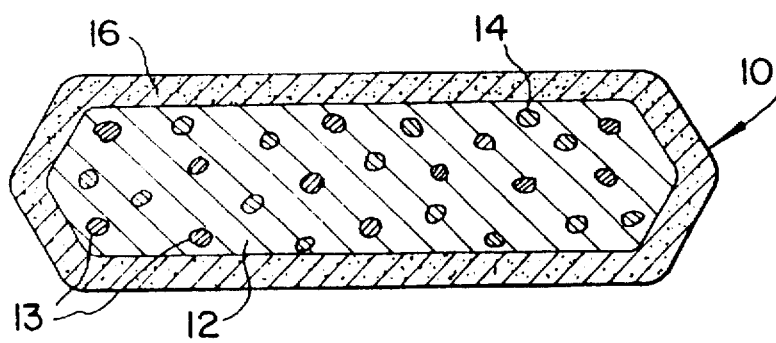
FIG. 3 is a cross sectional representation of a third embodiment of a tablet of the pharmaceutical composition described herein.

The pharmaceutical compositions of the present invention can be described with regard to the accompanying drawings, FIGS. 1, 2 and 3 schematically representing embodiments of the invention, the preferred embodiment being represented by the tablet of FIG. 1.

FIG. 1 represents a cross sectional view of a pharmaceutical composition herein. The pharmaceutical composition consists of a bilayer tablet (18) which can have any geometric shape, although for ease of description herein, an oval cross section is shown. The tablet (18) includes a naproxen layer (20) which includes, as the pharmaceutically active component, naproxen acid and other pharmaceutically acceptable excipients. The naproxen acid in the naproxen layer consists of an immediate release naproxen granulate (23) and a delayed release naproxen granulate (24). The naproxen layer (20) can be formulated by compression of the naproxen acid granulates with any suitable tableting equipment. Standard compression tableting techniques can be employed for forming the naproxen layer. The naproxen layer of the present invention can be prepared according to the methodology of Rotini and Marchi, U.S. Pat. No. 4,888,178, hereby incorporated by reference. The ratio of the immediate release naproxen granulate to the delayed release naproxen granulate can be as described in the U.S. Pat. No. 4,888,178 patent.

Adjacent to the naproxen layer (20) is a naproxen sodium layer (22) consisting of naproxen sodium and other pharmaceutically acceptable excipients. The naproxen sodium layer can be applied to the naproxen layer by compression or spraying techniques, such as are well known in the tableting art. The naproxen sodium in the naproxen sodium layer can be present in any therapeutically acceptable amount.

FIG. 2 represents an cross sectional view of an second embodiment of a pharmaceutical composition herein. The pharmaceutical composition consists of a trilayer tablet (26) which can have any geometric shape, although for ease of description herein, an oval cross section is shown. The tablet (26) includes a naproxen layer (30) which includes, as the pharmaceutically active component, naproxen acid and other pharmaceutically acceptable excipients. The naproxen acid in the layer consists of an immediate release naproxen granulate (31) and a delayed release naproxen granulate (32) as described above. The naproxen layer (30) can be formulated by compression of the naproxen acid granulates with any suitable tableting equipment. Standard compression tableting techniques can be employed for forming the naproxen layer.

Adjacent to the naproxen layer (30) are two layers (28) consisting of naproxen sodium and other pharmaceutically acceptable excipients. The naproxen sodium layers (28) can be applied by compression and spraying techniques, such as are well known in the tableting art. The naproxen sodium in the layer can be present in any therapeutically acceptable amount.

FIG. 3 represents a cross sectional view of a third embodiment of a pharmaceutical composition herein. The pharmaceutical composition consists of a tablet (10) which can have any geometric shape, although for ease of description herein an oval cross section is shown. The tablet (10) includes an inner core (12) which includes, as the pharmaceutically active component, naproxen acid and other pharmaceutically acceptable excipients. The naproxen acid in the core consists of an immediate release naproxen granulate (13) and a delayed release naproxen granulate (14) as described above. The core (12) can be formulated by compression of the naproxen acid granulates with any suitable tableting equipment. Standard compression tableting techniques can be employed for forming the core.

Surrounding the core is a coating (16) consisting of naproxen sodium and other pharmaceutically acceptable excipients. The coating can be applied by coating techniques, such as are well known in the tableting art. The naproxen sodium in the coating can be present in any therapeutically acceptable amount.

The naproxen acid in the naproxen layer can be present in any therapeutically acceptable amount. Naproxen is present in the naproxen layer in immediate and delayed release granulates in amounts effective for maintaining therapeutic blood levels of naproxen anions over a period of 24 hours. Naproxen administered independently is generally administered in therapeutic doses of about 500 to 1000 mg per day. The naproxen present in the naproxen layer of the pharmaceutical compositions herein can therefore be present in an amount to accomplish such dosing regimen in combination with the naproxen sodium of the immediate release layer. For the practice of the invention herein the amount of naproxen acid in the naproxen layer is generally present in an amount from about 20 to about 70 w/w % of the composition, and preferably from about 40 to about 80 w/w % and most preferably about 40 w/w %. Various pharmaceutically acceptable excipients can be combined with the naproxen acid granulates, as is well known in the pharmaceutical art.

The naproxen sodium in the naproxen sodium layer can be present in any therapeutically acceptable amount. Naproxen sodium administered independently is generally administered in therapeutic doses of 550–1100 mg per day. The naproxen sodium layer of the pharmaceutical composition herein is preferably in an amount to accomplish such dosing regimen in combination with the naproxen acid of the naproxen layer. The amount of naproxen sodium in the naproxen sodium layer is generally in an amount from about 15 to about 70 w/w % of the compositions of the present invention, preferably from about 20 to about 50 w/w % and more preferably from about 30 to about 35 w/w % and most preferably about 33 to 34 w/w %. Various pharmaceutically acceptable excipients can be combined with the naproxen sodium in the naproxen sodium layer as is well known in the pharmaceutical art.

In the preparation of the formulations of the present invention, an immediate release naproxen granulate is prepared by dry granulating the active agent naproxen with suitable adjuvant agents like binding, disintegrating and lubricating agents and then sifting the granules on a sieve having meshes of 1 mm.

Exemplary of such binding agents are polyvinylpyrrolidone, carboxymethylcellulose, microcrystalline cellulose, lactose, saccharose, mannitol, gumarabic, pectin, gelatin and the like.

Representative disintegrating agents include starch, sodium starch glycolate, alginates, polyvinylpyrrolidone and the like.

Examples of lubricating agents are talc, magnesium stearate, stearic acid, silica gel and the like.

A delayed release naproxen granulate is prepared by wet granulating the active agent with retarding agents by means of a solvent selected from an alcohol containing from 1 to 4 carbon atoms, an aromatic hydrocarbon, a ketone containing from 3 to 6 carbon atoms, an alkyl halide containing from 1 to 4 carbon atoms, mixtures thereof or mixtures thereof with water, then drying the granules in an oven at 50° C. and sifting them through a sieve having meshes of 1 mm. The preferred solvent being 95% ethyl alcohol.

Representative retarding agents are ethylcellulose, methylcellulose, polyvinylacetate, methacrylic acid esters, cellulose acetate, fatty alcohols containing from 12 to 32 carbon atoms, glyceric esters of fatty acids containing from 10 to 22 carbon atoms, like the mono- and di-stearate of glycerol, esters of fatty acids and alcohols having from 12 to 31 carbon atoms, paraffin, natural waxy substances like beeswax, unbleached wax, candelilla wax, carnauba wax, sealing wax, spermaceti, ozokerite and hydrogenated vegetable oils like hydrogenated castor oil, hydrogenated peanut oil, hydrogenated cotton seed oil and mixtures thereof.

Methylcellulose, ethylcellulose, hydrogenated vegetable oils and mixtures thereof are preferred retarding agents in the present invention.

The immediate release naproxen granulate and the delayed release naproxen granulate are mixed and compressed in such weight ratios that the active principle contained in the final naproxen layer is in the amounts described supra.

The immediate release naproxen sodium layer granulate is prepared by solubilizing polyvinylpyrrolidone in ethyl alcohol, adding a dye, mixing in the naproxen sodium, drying the granules in an oven and sifting them through a sieve having meshes of 1 mm.

The naproxen sodium layer particles are mixed with additional pharmaceutically acceptable excipients and compressed or sprayed onto the naproxen layer to form a naproxen sodium layer partially or entirely surrounding the naproxen layer, according to conventional methods well known in the tableting art.

The following examples 1–5 illustrate the methods used to prepare the compositions of the invention. These examples are given by way of illustration only and are not to be construed as limiting the invention in spirit or scope, as many modifications in materials and methods will be apparent from this disclosure to one having ordinary skill in the art.

EXAMPLE 1

A pharmaceutical composition consisting of an immediate and delayed release naproxen acid granulate layer and an immediate release naproxen sodium layer was prepared according to the following methodology. (This methodology results in a 2,000 tablet yield.)

A) Naproxen sodium granulate (for the naproxen sodium layer)

| | |
|---|---|
| Naproxen sodium | 300 g. |
| PVP K30 | 12 |
| Dye (yellow) E 102 | 2 |
| Ethyl alcohol | 45 |

PVP K30 was solubilized in 45 grams of ethyl alcohol, the dye was added and mixed with the naproxen sodium for 5 minutes in a mixer. The mixture was granulated by extrusion and dried in an oven at 35° C. The dried product was sifted on a 1 mm size sieve.

B) Naproxen acid granulate (immediate release)

| | |
|---|---|
| Naproxen acid | 130 g. |
| Starch | 13 |
| Lactose | 38.48 |
| Sodium starch glycolate | 7.8 |
| PVP K90 | 7.8 |
| Magnesium stearate | 0.52 |
| 95% ethyl alcohol | 3.458 |

The powders were mixed for 15 minutes in a granulator. Ethyl alcohol was sprayed onto the powder mixture and mixing was continued for 10 minutes. The dried granulation was then passed through a 1.25 mm sieve.

C) Naproxen acid granulate (delayed release)

| | |
|---|---|
| Naproxen acid | 1000 g. |
| Ethyl-cellulose | 120 |
| Hydrogenated castor oil | 380 |
| Ethyl alcohol | 402.24 |

The powders were mixed for 60 minutes in a mixer and then mixed with ethyl alcohol for 10 minutes. Granulation was done by extrusion and was dried at 50° C. The dried product was sifted using a 1 mm sieve.

D) Formation of the naproxen layer

The immediate release and delayed release granulates of naproxen acid were mixed with PVP CL micrionized (68 g.) for 10 minutes. The granulation mixture was compressed with a suitable punch to form a layer of naproxen acid.

E) Compression of the naproxen layer with the naproxen sodium layer

The naproxen layer was compressed with naproxen sodium granulate using a suitable punch to form a bilayered tablet having separate layers of naproxen and naproxen sodium.

EXAMPLE 2

A pharmaceutical composition was prepared consisting of an immediate and delayed release naproxen acid granulate layer and an immediate release naproxen sodium layer according to the method of Example 1. The tablet had the following composition:

| NAPROXEN SODIUM LAYER | |
|---|---|
| Naproxen Sodium | mg 150 |
| PVP K 30 | mg 6 |
| Yellow Dye E 102 | mg 1 |

| NAPROXEN LAYER | |
|---|---|
| Cornstarch | mg 8.16 |
| Lactose | mg 24.18 |
| Sodium starch glycolate | mg 4.92 |
| PVP K 90 | mg 4.92 |
| Magnesium stearate | mg 0.33 |
| Hydrogenated castor oil | mg 140.22 |
| Ethyl cellulose | mg 44.28 |
| PVP C.L. | mg 20.4 |
| Naproxen Acid | mg 450 |
| Total Weight | mg 854.41 |

EXAMPLE 3

A pharmaceutical composition was prepared consisting of an immediate and delayed release naproxen acid granulate layer and an immediate release naproxen sodium layer according to the method of example 1. The tablet had the following composition:

| NAPROXEN SODIUM LAYER | |
|---|---|
| Naproxen Sodium | mg 150 |
| PVP K 30 | mg 6 |
| Yellow Dye E 102 | mg 1 |

| NAPROXEN LAYER | |
|---|---|
| Cornstarch | mg 6.5 |
| Lactose | mg 19.24 |
| Sodium glycolate starch | mg 3.9 |
| PVP K 90 | mg 3.9 |
| Magnesium stearate | mg 0.26 |
| Hydrogenated castor oil | mg 190 |
| Ethylcellulose | mg 60 |
| PVP C.L. | mg 34 |
| Naproxen Acid | mg 565 |
| Total Weight | mg 1039.80 |

EXAMPLE 4

A pharmaceutical composition was prepared consisting of an immediate and delayed release naproxen acid granulate layer and an immediate release naproxen sodium layer according to the method of example 1. The tablet had the following composition:

| NAPROXEN SODIUM LAYER | |
|---|---|
| Naproxen Sodium | mg 179.1 |
| PVP K 30 | mg 7.1 |
| Yellow Dye E 102 | mg 0.18 |
| PVP C.L. | mg 7.5 |
| Magnesium Stearate | mg 1.9 |

| NAPROXEN LAYER | |
|---|---|
| Cornstarch | mg 2.4 |
| Lactose | mg 7.1 |
| Sodium glycolate starch | mg 1.4 |
| PVP K 90 | mg 1.4 |
| Magnesium stearate | mg 0.05 |
| Hydrogenated castor oil | mg 71.2 |
| Ethylcellulose | mg 22.5 |

-continued

| | |
|---|---|
| PVP C.L. | mg 12.7 |
| Naproxen Acid | mg 211.5 |
| Total Weight | mg 526 |

EXAMPLE 5

A pharmaceutical composition was prepared consisting of an immediate and delayed release naproxen acid granulate layer and an immediate release naproxen sodium layer according to the method of example 1. The tablet had the following composition:

| NAPROXEN SODIUM LAYER | |
|---|---|
| Naproxen Sodium | mg 238.8 |
| PVP K 30 | mg 9.5 |
| Yellow Dye E 102 | mg 0.24 |
| PVP C.L. | mg 9.9 |
| Magnesium Stearate | mg 2.6 |

| NAPROXEN LAYER | |
|---|---|
| Cornstarch | mg 3.2 |
| Lactose | mg 9.5 |
| Sodium glycolate starch | mg 1.9 |
| PVP K 90 | mg 1.9 |
| Magnesium stearate | mg 0.06 |
| Hydrogenated castor oil | mg 95.0 |
| Ethylcellulose | mg 30.0 |
| PVP C.L. | mg 16.9 |
| Naproxen Acid | mg 282.0 |
| Total Weight | mg 701.5 |

Pharmacokinetic tests have been carried out in man to verify the onset and duration of naproxen plasma levels for the above described formulations. These pharmacokinetic tests have been performed on groups each consisting of six healthy volunteers, by examining the hematic levels of naproxen at various time points from 0.3 up to 72 hours after the administration of the compositions.

The values reported in the following Tables I and II are calculated from the mean of the values of the single values of the six healthy volunteers. The naproxen was checked in the plasma by spectrophotometric methodology at 272 nm after passing through a high pressure liquid chromatography column (HPLC); the values are expressed in mcg/ml of plasma.

TABLE I

Hematic Levels of Naproxen
Formulation of Example 3

| Time (hrs) | Hematic Levels of Naproxen (mean value mcg/ml) |
|---|---|
| 0.3 | 34.2 |
| 0.6 | 41.7 |
| 1 | 50.2 |
| 2 | 57.4 |
| 3 | 63.0 |
| 4 | 61.1 |
| 6 | 56.1 |
| 8 | 50.8 |
| 12 | 45.3 |
| 24 | 33.0 |

TABLE I-continued

Hematic Levels of Naproxen
Formulation of Example 3

| Time (hrs) | Hematic Levels of Naproxen (mean value mcg/ml) |
|---|---|
| 48 | 13.5 |
| 72 | 5.7 |

TABLE II

Hematic Levels of Naproxen
Formulation of Example 2

| Time (hrs) | Hematic Levels of Naproxen (mean value mcg/ml) |
|---|---|
| 0.5 | 37.0 |
| 1 | 49.8 |
| 2 | 57.1 |
| 3 | 59.7 |
| 4 | 59.4 |
| 6 | 50.6 |
| 8 | 44.5 |
| 12 | 35.7 |
| 24 | 21.6 |
| 48 | 7.7 |
| 72 | 3.2 |

Figure 4:
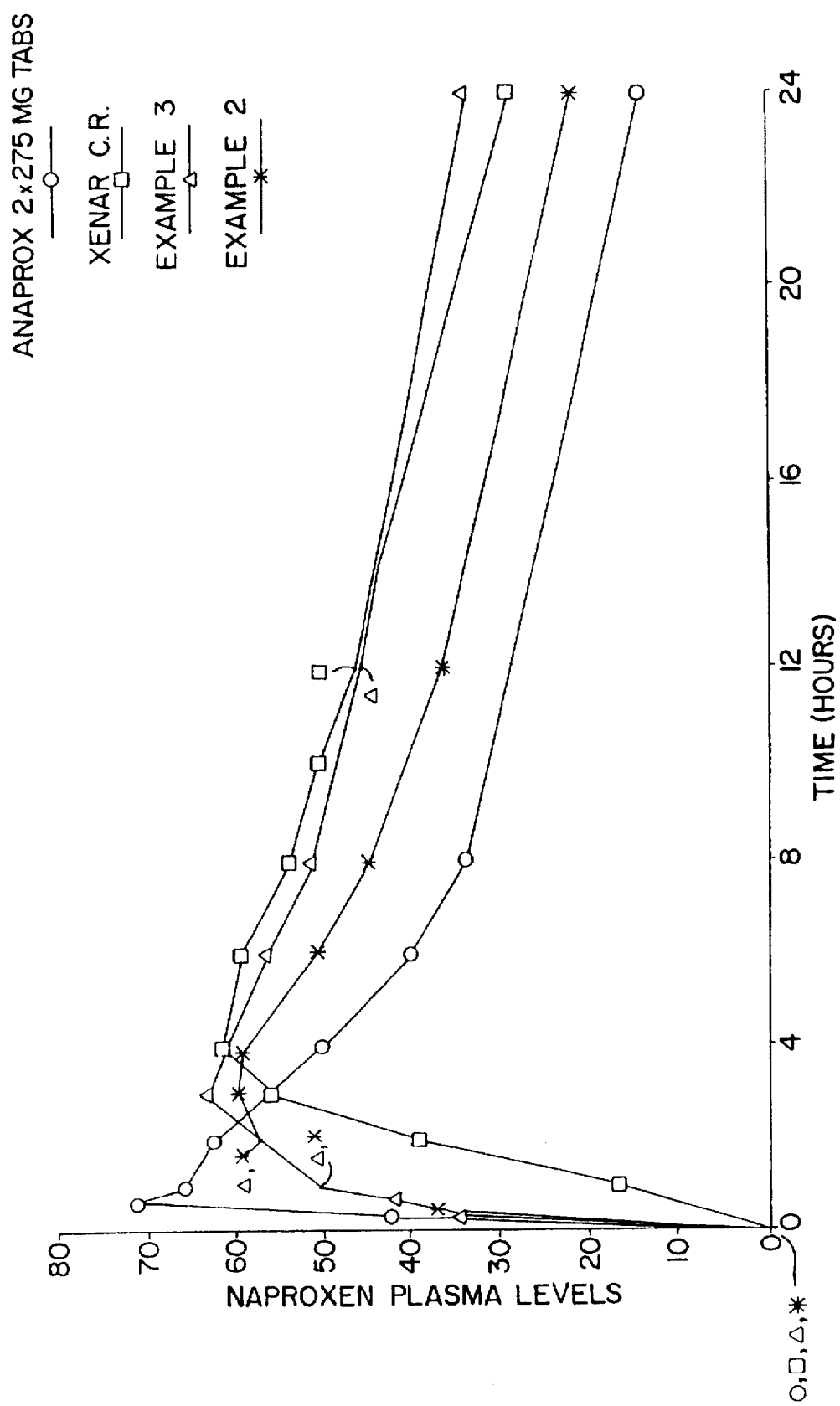
FIG. 4 is a graphical representation of the plasma profiles of two different naproxen and naproxen sodium controlled release formulations, of an immediate release naproxen sodium formulation and of a controlled release naproxen acid formulation, over 24 hours.

FIG. 4 is a graphical representation of the plasma profile of two formulations of controlled release naproxen and naproxen sodium, of an immediate release formulation of naproxen sodium and a controlled release naproxen formulation, over 24 hours. FIG. 5 is an enlargement of the plasma profiles for the same four formulations for the initial four hours, after administration.

It is shown in FIGS. 4 and 5 that the compositions of the present invention, Examples 2 and 3 reach therapeutic blood plasma levels in less than one hour. FIG. 4 shows that the compositions of Examples 2 and 3 maintain therapeutic blood levels over a period of 24 hours.

FIG. 4 shows that Anaprox®, (described in the Physician's Desk Reference, 46th edition 1992, as an immediate release naproxen sodium tablet, commercially available from Syntex) achieves therapeutic blood levels within 0.5 hours but as shown in FIG. 4, the therapeutic blood levels are not maintained over a period of 24 hours and thus that composition would not be useful for once daily administration. Xenar, CR (a controlled release naproxen acid tablet, commercially available in Italy from Alfa Pharmaceuticals) as is shown in FIG. 5, does not achieve therapeutic blood levels for almost two hours and thus would not be useful for immediate relief from pain.

A particularly beneficial aspect of the invention herein, as shown in the graphs, is that the immediate release naproxen sodium layer allows for faster absorption thereby providing for pain relief within an hour. FIG. 4 shows the added benefit that the controlled release layer of naproxen acid maintains the therapeutic blood levels for a duration of 24 hours thereby providing for once daily administration. Additionally, the design of the tablet provides for total disintegration of the tablet thereby reducing the potential for gastric irritation and damage.

What is claimed is:

1. A controlled release pharmaceutical composition comprising:

a layer of naproxen acid; and an outer layer of naproxen sodium adjacent to the naproxen acid layer which achieves therapeutic plasma levels of naproxen in less than one hour wherein the naproxen acid is present in an amount from about 20 to about 70 w/w % and the naproxen sodium is present in an amount from about 15 to about 70 w/w %.

2. A controlled release pharmaceutical composition according to claim 1 wherein the naproxen acid layer comprises:

an immediate release granulate of naproxen acid; and a delayed release granulate of naproxen acid.

3. A controlled release pharmaceutical composition according to claim 2 wherein the naproxen sodium is present in an amount from about 20–50 w/w % of the composition.

4. A controlled release pharmaceutical composition according to claim 3 wherein the naproxen acid is present in an amount from about 40–80 w/w % of the composition.

5. A controlled release pharmaceutical composition according to claim 4 wherein the naproxen sodium is present in an amount from about 30–35 w/w % of the composition.

6. A controlled release pharmaceutical composition according to claim 5 wherein the naproxen acid is present in an amount of about 40 w/w % of the composition.

7. A controlled release pharmaceutical composition according to claim 6 wherein the naproxen sodium is present in an amount of about 35 w/w % of the composition.

8. A controlled release pharmaceutical composition comprising:

a layer of naproxen acid comprised of an immediate release granulate of naproxen acid and a delayed release granulate of naproxen acid; and a layer of naproxen sodium adjacent to the naproxen acid layer;

wherein the naproxen acid is present in an amount from about 20 to about 70 w/w % and the naproxen sodium is present in an amount from about 15 to about 70 w/w %.

9. A controlled release pharmaceutical composition according to claim 8 wherein the naproxen acid in the immediate release granulate is present in an amount up to about 10%.

10. A controlled release pharmaceutical composition according to claim 9 wherein the naproxen acid present in the delayed release granulate is present in an amount from about 20 to about 50 w/w %.

11. A method of treating mild to moderate pain comprising administering a controlled release pharmaceutical composition comprising:

a layer of naproxen acid; and a layer of naproxen sodium adjacent to the naproxen acid layer.

12. A method according to claim 11 wherein the naproxen acid layer comprises:

an immediate release granulate of naproxen acid; and a delayed release granulate of naproxen acid.

13. A method according to claim 12 wherein the pain is associated with dysmenorrhea.

14. A method according to claim 12 wherein the pain is associated with arthritis.

* * * * *